(12) United States Patent
Souvie

(10) Patent No.: US 6,818,788 B2
(45) Date of Patent: Nov. 16, 2004

(54) METHOD FOR SYNTHESIS OF N-[(S)-1-CARBOXYBUTYL]-(S)-ALANINE ESTERS AND USE IN SYNTHESIS OF PERINDOPRIL

(75) Inventor: Jean-Claude Souvie, Le Havre (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/221,973

(22) PCT Filed: Mar. 30, 2001

(86) PCT No.: PCT/FR01/00959

§ 371 (c)(1),
(2), (4) Date: Sep. 16, 2002

(87) PCT Pub. No.: WO01/56353

PCT Pub. Date: Aug. 9, 2001

(65) Prior Publication Data

US 2003/0045744 A1 Mar. 6, 2003

(30) Foreign Application Priority Data

Mar. 31, 2000 (FR) .............................. 00 04112

(51) Int. Cl.⁷ .......................................... C07C 229/00
(52) U.S. Cl. ...................................................... 560/171
(58) Field of Search ............................... 548/452, 492; 560/171

(56) References Cited

U.S. PATENT DOCUMENTS

| | | | | | |
|---|---|---|---|---|---|
| 4,247,716 A | * | 1/1981 | Kiyoura | .................. | 562/513 |
| 4,914,214 A | * | 4/1990 | Vincent et al. | .............. | 548/492 |
| 2003/0109743 A1 | * | 6/2003 | Souvie et al. | ................ | 560/171 |

FOREIGN PATENT DOCUMENTS

EP      0 308 341    * 3/1989

OTHER PUBLICATIONS

Vincent et al, "Stereoselective Synthesis of a New Perhydroindole Derivative of Chiral Iminodiacid, a Potent Inhibitor of Angiotensin Converting Enzyme" Tetrahedron Letters, vol. 23(16), pp. 1677–1680 (1982).*

Yamada and Hashimoto, "Asymmetric Transamination from Amino Acids (I) Asymmetric Synthesis of Amino Acids to alpha–Ke Acid" Tetrahedron Letters, vol. 13, pp. 997–1000 (1982).*

Hayashi et al, "Computer–assisted automated synthesis. III. Synthesis of substituted N–(carboxyalkyl) amino–acid tert-butyl este derivatives" Journal of Automatic Chemistry, vol. 13(5)), pp. 187–197 (Sep.–Oct. 1991).*

* cited by examiner

*Primary Examiner*—Richard L. Raymon
*Assistant Examiner*—Zachary C. Tucker
(74) *Attorney, Agent, or Firm*—The Firm of Hueschen and Sage

(57) ABSTRACT

Stereoselective process for the industrial synthesis of compounds of formula (I):

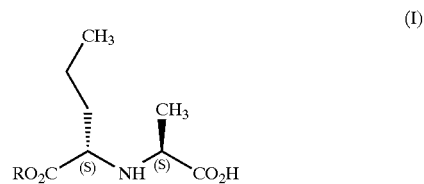

wherein R represents linear or branched ($C_1$–$C_6$)alkyl.

Application in the synthesis of perindopril and pharmaceutically acceptable salts thereof.

5 Claims, No Drawings

METHOD FOR SYNTHESIS OF N-[(S)-1-CARBOXYBUTYL]-(S)-ALANINE ESTERS AND USE IN SYNTHESIS OF PERINDOPRIL

This application was filed under 35 U.S.C. 371, and is the U.S. National Stage of PCT/FR01/00959.

The present invention relates to a process for the industrial synthesis of N-[(S)-1-carboxybutyl]-(S)-alanine esters, and to their application in the industrial synthesis of perindopril and its pharmaceutically acceptable salts.

More specifically, the present invention relates to a new process for the industrial synthesis of the compounds of formula (I):

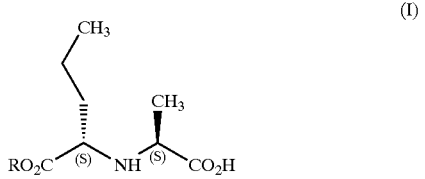

wherein R represents a linear or branched $(C_1-C_6)$alkyl group,
and addition salts thereof with a mineral or organic acid or base. The compounds of formula (I) obtained in accordance with the process of the invention are useful in the synthesis of perindopril of formula (II):

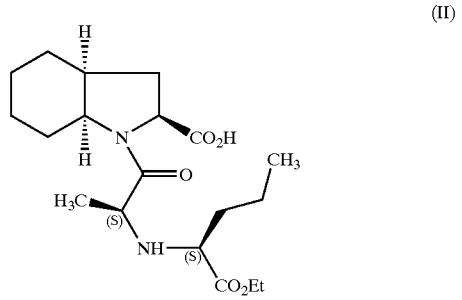

and in the synthesis of pharmaceutically acceptable salts thereof.

Perindopril and salts thereof have valuable pharmacological properties. Their principal property lies in the inhibition of the enzyme that converts angiotensin I (or kininase II), which enables on the one hand prevention of the conversion of the decapeptide angiotensin I to the octapeptide angiotensin II (vasoconstrictor) and on the other hand prevention of the degradation of bradykinin (vasodilator) to inactive peptide. Those two actions contribute to the beneficial effects of perindopril in cardiovascular disorders, especially arterial hypertension and cardiac insufficiency.

Perindopril, its preparation and its therapeutic use have been described in European Patent Specification EP 0 049 658.

Given the pharmaceutical interest in that compound, it is important to be able to obtain the intermediate of formula (I) by an effective industrial synthesising process that allows especially the selective production of the (S,S) diastereoisomer in a good yield and with an excellent degree of purity but that can equally readily be performed on an industrial scale.

Some methods for the preparation of the compounds of formula (I) are already known, but on an industrial scale those processes have significant disadvantages:

The journal Tet. Lett. 1982, 23 (16), 1677–80 describes the production of a compound of formula (I) (R=ethyl) by reacting ethyl 2-oxovalerate with alanine tert-butyl ester in ethanol in the presence of sodium cyanoborohydride, but that reducing agent is particularly toxic, very hygroscopic and difficult to handle on an industrial scale.

The patent specification EP 0 309 324 describes obtaining a compound of formula (I) (R=ethyl) by reacting alanine benzyl ester with ethyl α-bromovalerate in dimethylformamide in the presence of triethylamine. The major drawbacks of that process are the large number of steps involved and the low yield of the (S,S) isomer. Indeed, since the reaction is not diastereoselective, in order to obtain the pure (S,S) isomer it requires the addition of a purification step, which comprises fractional crystallisation in the presence of maleic acid.

The patent specifications EP 0 308 340 and EP 0 308 341 (equivalent to U.S. Pat. No. 4,914,214, the subject matter of which is hereby incorporated by reference) describe the production of a compound of formula (I) (R=ethyl) by reacting ethyl norvalinate hydrochloride with pyruvic acid in water in the presence of hydrogen, palladium-on-carbon and sodium hydroxide. The isolation of the crude product is then carried out by evaporation of the water, then ethanol is added to precipitate the sodium chloride formed during the reaction. After filtration, the ethanol solution obtained is evaporated and the residue is recrystallised from acetonitrile. That process has the advantage of resulting in a compound of formula (I) that has excellent optical purity: only the (S,S) diastereoisomer crystallises under those conditions. Furthermore, the use of pyruvic acid as reagent, a low-cost, industrially available, natural product, and the use of water as the reaction solvent, are particularly advantageous. On the other hand, however, a disadvantage of that process is that its use on an industrial scale is particularly laborious: the isolation of the reaction product is in fact effected by the evaporation of a large quantity of water and then requires a series of operations (addition of a first organic solvent, filtration, evaporation, and then recrystallisation from a second organic solvent) for the product to be obtained in chemically and optically pure form.

The Applicant has now developed a new process for the industrial synthesis of compounds of formula (I) that combines the advantages of hydrogenation in aqueous medium with a particularly rapid and simple isolation for use on an industrial scale.

More specifically, the present invention relates to a process for the industrial synthesis of compounds of formula (I) which is characterised in that sodium pyruvate of formula (III):

is condensed with a compound of formula (IV):

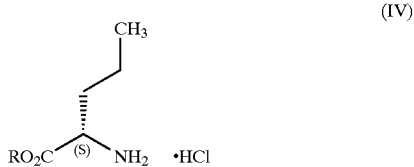

wherein R is as defined for formula (I),
with hydrogenation catalysed by 5% palladium-on-carbon, in water, at a pressure of from 1 to 20 bar, preferably from 1 to 5 bar, at a temperature of from 10 to 60° C., preferably from 10 to 40° C., in the presence of sodium hydroxide in an amount of from 0.1 to 0.2 mol per mol of compound of formula (IV) used, in order to yield the compound of formula (I) directly, in optically pure form, following acidification of the reaction mixture to a pH of from 2.8 to 4.5, preferably from 3 to 3.5, and then filtration.

A low hydrogen pressure unexpectedly results in a yield and a chemical and enantiomeric purity that are as good as when the reaction is carried out at elevated pressure.

Surprisingly, the single precipitation after acidification of the aqueous reaction mixture yields the single (S,S) isomer with good chemical purity and excellent enantiomeric purity.

The recrystallisation step can thus be omitted, making the isolation particularly quick and simple to apply on an industrial scale.

The Example below illustrates the invention but does not limit it in any way.

EXAMPLE

N-[(S)-ethoxycarbonyl-1-butyl]-(S)-alanine

Into a tank, fitted with a stirrer, introduce 3 kg of ethyl S-norvalinate hydrochloride dissolved in water, 0.61 of an aqueous 4N sodium hydroxide solution and 2 kg of sodium pyruvate. Into a hydrogenation apparatus introduce 5% palladium-on-carbon suspended in water, then the solution obtained above. Hydrogenate at 35° C. at a pressure of 1.2 bar until the theoretical amount of hydrogen has been absorbed. Remove the catalyst by filtration, then add concentrated hydrochloric acid to the filtrate until a pH of 3.1 is obtained. Cool to from 0 to 5° C., then harvest the resulting solid by means of filtration. Wash the cake with iced acetonitrile and dry to constant weight at 40° C. in a fan oven. N-[(S)-ethoxycarbonyl-1-butyl]-(S)-alanine is thereby obtained in a yield of 62%, with a chemical purity of 95% and an enantiomeric purity exceeding 99%.

I claim:

1. A process for the synthesis of the compounds of formula (I)

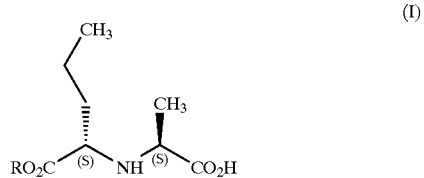

wherein R represents linear or branched $(C_1-C_6)$alkyl, wherein sodium pyruvate of formula (III):

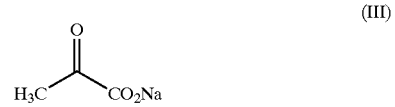

is condensed with a compound of formula (IV):

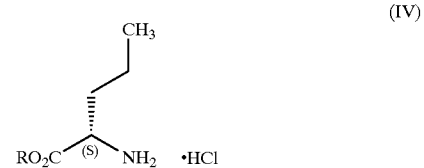

wherein R is as defined for formula (I),
with hydrogenation catalysed by 5% palladium-on-carbon,
in water,
at a pressure of 1 to 20 bar,
at a temperature of 10 to 60° C.,
in the presence of sodium hydroxide in an amount of 0.1 to 0.2 mol per mol of compound of formula (IV) used, to yield the compound of formula (I) directly, in optically pure form, following acidification of the reaction mixture to a pH of 2.8 to 4.5 and then filtration.

2. The process of claim 1 for producing the compound of formula (I), wherein R represents ethyl.

3. The process of claim 1, wherein the hydrogenation pressure is 1 to 5 bar.

4. The process of claim 1, wherein the hydrogenation temperature is 10 to 40° C.

5. The process of claim 1, wherein the pH after acidification is 3 to 3.5.

* * * * *

UNITED STATES PATENT AND TRADEMARK OFFICE
CERTIFICATE OF CORRECTION

PATENT NO. : 6,818,788 B2
DATED : November 16, 2004
INVENTOR(S) : Jean-Claude Souvie It is certified that error appears in the above-identified patent and that said Letters Patent is hereby corrected as shown below:

<u>Title page,</u>
Item [56], References Cited, FOREIGN PATENT DOCUMENTS,
"EP 0 308 341" should be -- EP 0 308 340 --

Signed and Sealed this

Twenty-fourth Day of May, 2005

JON W. DUDAS
*Director of the United States Patent and Trademark Office*